United States Patent [19]

Suchy et al.

[11] Patent Number: 5,266,554
[45] Date of Patent: Nov. 30, 1993

[54] HETEROCYCLIC COMPOUNDS

[75] Inventors: Milos Suchy, Kaiseraugst; Jean Wenger, Uster; Paul Winternitz, Greifensee; Martin Zeller, Baden, all of Switzerland

[73] Assignee: Ciba-Geiby Corporation, Ardsley, N.Y.

[21] Appl. No.: 990,826

[22] Filed: Dec. 14, 1992

Related U.S. Application Data

[63] Continuation of Ser. No. 750,365, Aug. 27, 1991, abandoned.

[30] Foreign Application Priority Data

Aug. 31, 1990 [CH] Switzerland ............. 2832/90

[51] Int. Cl.$^5$ ............... C07D 239/54; C07D 239/70; A01N 43/54
[52] U.S. Cl. ............... 504/243; 504/240; 544/311; 544/312; 544/253
[58] Field of Search ........ 544/311, 312, 253; 504/243, 240

[56] References Cited

U.S. PATENT DOCUMENTS

| | | | |
|---|---|---|---|
| 4,746,352 | 5/1988 | Wenger | 71/90 |
| 4,812,164 | 3/1989 | Wenger | 71/92 |
| 4,859,229 | 8/1989 | Wenger | 71/92 |
| 4,919,704 | 4/1990 | Moser | 71/96 |
| 4,941,909 | 7/1990 | Wenger | 71/92 |
| 5,041,156 | 8/1991 | Suchy | 71/92 |

OTHER PUBLICATIONS

Suchy et al., Chemical Abstracts, vol. 115, entry 29370z (1991).

*Primary Examiner*—John M. Ford
*Attorney, Agent, or Firm*—George R. Dohmann

[57] ABSTRACT

The invention relates to novel compounds of the formula

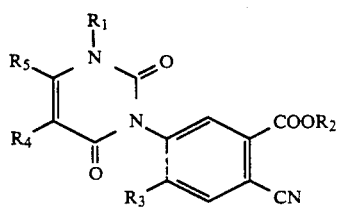

wherein $R_1$, $R_2$, $R_3$, $R_4$ and $R_5$ have the meanings given in the description, to enol ethers and salts thereof and their preparation, to weed control compositions that comprise such compounds as active ingredients, and to the use of the compounds or compositions to control weeds. The invention relates also to certain novel starting materials and to the preparation thereof.

9 Claims, No Drawings

HETEROCYCLIC COMPOUNDS

This application is a continuation, now abandoned, of application Ser. No. 07/750,365, filed Aug. 27, 1991.

The present invention relates to heterocyclic compounds, that is to 3-aryluracils of the general formula

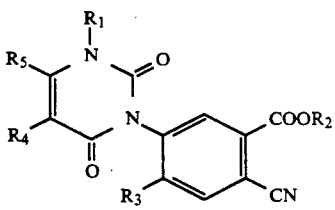

wherein $R_1$ is hydrogen, $C_1$-$C_4$alkyl, $C_3$-$C_4$alkenyl, $C_3$-$C_4$alkynyl, $C_2$-$C_6$alkoxyalkyl or $C_1$-$C_4$haloalkyl, $R_2$ is hydrogen, $C_1$-$C_6$alkyl, $C_2$-$C_6$alkoxyalkyl, $C_4$-$C_7$cycloalkenyl-$C_1$-$C_4$alkyl that is unsubstituted or ring-substituted by from 1 to 3 $C_1$-$C_3$alkyl groups, $C_3$-$C_4$alkenyl, $C_4$-$C_7$cycloalkenyl-$C_3$-$C_5$alkenyl that is unsubstituted or ring-substituted by from 1 to 3 $C_1$-$C_3$alkyl groups, aryl-$C_3$-$C_5$alkenyl, $C_3$-$C_4$alkynyl, $C_4$-$C_7$cycloalkenyl-$C_3$-$C_5$alkynyl that is unsubstituted or ring-substituted by from 1 to 3 $C_1$-$C_3$alkyl groups, or aryl-$C_3$-$C_5$-alkynyl, $R_3$ is hydrogen or halogen, $R_4$ is hydrogen, halogen or $C_1$-$C_4$alkyl and $R_5$ is $C_1$-$C_4$alkyl or $C_1$-$C_4$haloalkyl, or $R_4$ and $R_5$ together are tri- or tetra-methylene, with the proviso that, when $R_5$ is $C_1$-$C_4$haloalkyl, $R_1$ is other than $C_1$-$C_4$haloalkyl and $R_2$ is other than hydrogen, and the corresponding enol ethers of those compounds of formula I wherein $R_1$ is other than hydrogen or $C_1$-$C_4$haloalkyl, and salts of those compounds of formula I wherein $R_1$ and/or $R_2$ are (is) hydrogen.

There are thus to be understood by the above-mentioned enol ethers the compounds of the formula

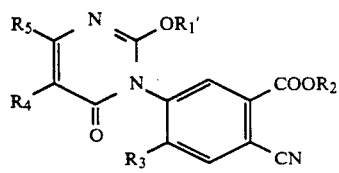

wherein $R_1'$ is $C_1$-$C_4$alkyl, $C_3$-$C_4$alkenyl, $C_3$-$C_4$alkynyl or $C_2$-$C_6$alkoxyalkyl.

The compounds of the invention, that is to say the compounds of formula I and the enol ethers and salts thereof, are herbicidally active and are suitable as active ingredients of weed control compositions. The invention thus also includes weed control compositions that contain compounds of the invention as active ingredients, processes for the preparation of those compounds and the use of the compounds and compositions for controlling weeds.

In the above formula I, "halogen" includes fluorine, chlorine, bromine and iodine. The alkyl, alkenyl and alkynyl radicals may be straight-chain or branched, this applying also to the or each alkyl, alkenyl or alkynyl moiety of the various alkyl-, alkenyl- or alkynyl-containing groups, respectively, such as, for example, "$C_4$-$C_7$cycloalkenyl-$C_3$-$C_5$-alkenyl that is unsubstituted or ring-substituted by from 1 to 3 $C_1$-$C_3$alkyl groups". A haloalkyl group may contain one or more identical or different halogen atoms. Aryl (of the aryl-$C_3$-$C_5$alkenyl and aryl-$C_3$-$C_5$alkynyl groups) is especially phenyl, it being possible for such groups to be substituted by from 1 to 3 halogen atoms, $C_1$-$C_3$alkyl, $C_1$-$C_3$haloalkyl, $C_1$-$C_3$alkoxy, $C_1$-$C_3$alkylthio, $C_2$-$C_4$alkanoyl, $C_2$-$C_4$alkoxycarbonyl, $C_1$-$C_3$alkylsulfonyl, nitro and/or cyano. The fused rings formed by $R_4$ and $R_5$ ($R_4$ and $R_5$ together are tri- or tetra-methylene) are represented by the following partial structures:

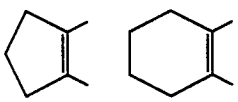

The salts of the compounds of formula I are especially alkali metal salts, e.g. sodium and potassium salts; alkaline earth metal salts, e.g. calcium and magnesium salts; ammonium salts, i.e. unsubstituted ammonium salts and mono- or poly-substituted ammonium salts, e.g. triethylammonium and methylammonium salts, and also salts with other organic bases, e.g. with pyridine.

The possible presence of at least one asymmetric carbon atom in the compounds of formula I means that the compounds may occur in optically isomeric forms. As a result of the possible presence of an aliphatic C=C double bond, geometric isomerism may also occur. Formula I shall include all those possible isomeric forms and also mixtures thereof.

If $R_1$ or $R_2$ is alkenyl or alkynyl, then that group is preferably allyl or 3-buten-2-yl, or propargyl or 3-butyn-2-yl, respectively. In general, a halogen atom that may be present is preferably fluorine.

Independently of one another, $R_1$ is preferably $C_1$-$C_4$alkyl, especially methyl; $R_2$ is preferably $C_1$-$C_6$alkyl, $C_2$-$C_6$alkoxyalkyl, $C_3$-$C_4$alkenyl or $C_3$-$C_4$alkynyl; $R_3$ is preferably hydrogen or fluorine; $R_4$ is preferably hydrogen, methyl or fluorine; and $R_5$ is preferably $C_1$-$C_4$alkyl or trifluoromethyl. Likewise, $R_4$ and $R_5$ together are preferably tri- or tetramethylene.

Especially preferred compounds of formula I are:

2-cyano-5-(1,2,4,5,6,7-hexahydro-1-methyl-2,4-dioxo-3H-cyclopenta[d]pyrimidin-3-yl)-benzoic acid isopropyl ester, 2-cyano-4-fluoro-5-(1,2,4,5,6,7-hexahydro-1-methyl-2,4-dioxo-3H-cyclopenta[d]pyrimidin-3-yl)-benzoic acid isopropyl ester, 2-cyano-5-[1,4,5,6,7,8-hexahydro-1-methyl-2,4-dioxo-3(2H)-quinazolinyl]-benzoic acid isopropyl ester, 2-cyano-4-fluoro-5-[1,4,5,6,7,8-hexahydro-1-methyl-2,4-dioxo-3(2H)-quinazolinyl]-benzoic acid isopropyl ester, 2-cyano-5-[3,6-dihydro-3,4-dimethyl-2,6-dioxo-1(2H)-pyrimidinyl]-4-fluorobenzoic acid isopropyl ester, 2-cyano-5-[3,6-dihydro-3-methyl-4-trifluoromethyl-2,6-dioxo-(1(2H)-pyrimidinyl]-benzoic acid isopropyl ester and 2-cyano-5-[3,6-dihydro-3-methyl-4-trifluoromethyl-2,6-dioxo-1(2H)-pyrimidinyl]-4-fluorobenzoic acid isopropyl ester, and the corresponding methyl, ethyl, n-propyl, n-butyl, sec-butyl, isobutyl, tert-butyl, methoxymethyl, 1-methoxyethyl, 2-methoxyethyl, 1-methoxypropyl, 1-ethoxyethyl, 2-methoxy-1-methylethyl, allyl, 1-methyl-2-propenyl, 1-ethyl-2-propenyl, 2-butenyl, propargyl, 2-butynyl, 1-methyl-2-propynyl- and 1-ethyl-2-propynyl esters of the above compounds.

Further examples of compounds of formula I are:

2-cyano-4-fluoro-5-[5-chloro-3,6-dihydro-4-methyl-2,6-dioxo-1(2H)-pyrimidinyl]-benzoic acid isopropyl ester, 2-cyano-4-fluoro-5-[5-chloro-3,6-dihydro-3,4-dimethyl-2,6-dioxo-1(2H)-pyrimidinyl]-benzoic acid isopropyl ester, 2-cyano-4-fluoro-5-[3,6-dihydro-4-trifluoromethyl-2,6-dioxo-1(2H)-pyrimidinyl]-benzoic acid isopropyl ester, 2-cyano-4-fluoro-5-[4-ethyl-3,6-dihydro-2,6-dioxo-1(2H)-pyrimidinyl]-benzoic acid isopropyl ester, 2-cyano-4-fluoro-5-[4-ethyl-3,6-dihydro-3-methyl-2,6-dioxo-1(2H)-pyrimidinyl]-benzoic acid isopropyl ester, 2-cyano-4-fluoro-5-[3,4-diethyl-3,6-dihydro-2,6-dioxo-1(2H)-pyrimidinyl]-benzoic acid isopropyl ester, 2-cyano-4-fluoro-5-[4-ethyl-3,6-dihydro-5-methyl-2,6-dioxo-1(2H)-pyrimidinyl]-benzoic acid isopropyl ester, 2-cyano-4-fluoro-5-[4-ethyl-3,6-dihydro-3,5-dimethyl-2,6-dioxo-1(2H)-pyrimidinyl]-benzoic acid isopropyl ester, 2-cyano-4-fluoro-5-[3,4-diethyl-3,6-dihydro-5-methyl-2,6-dioxo-1(2H)-pyrimidinyl]-benzoic acid isopropyl ester, 2-cyano-4-fluoro-5-[3,6-dihydro-4-isopropyl-2,6-dioxo-1(2H)-pyrimidinyl]-benzoic acid isopropylester, 2-cyano-4-fluoro-5-[3,6-dihydro-4-isopropyl-3-methyl-2,6-dioxo-1(2H)-pyrimidinyl]-benzoic acid isopropyl ester, 2-cyano-4-fluoro-5-[3-ethyl-3,6-dihydro-4-isopropyl-2,6-dioxo-1(2H)-pyrimidinyl]-benzoic acid isopropyl ester, 2-cyano-4-fluoro-5-[3,6-dihydro-4-isopropyl-5-methyl-2,6-dioxo-1(2H)-pyrimidinyl]-benzoic acid isopropyl ester, 2-cyano-4-fluoro-5-[3,6-dihydro-3,5-dimethyl-4-isopropyl-2,6-dioxo-1(2H)-pyrimidinyl]-benzoic acid isopropyl ester, 2-cyano-4-fluoro-5-[3-ethyl-3,6-dihydro-4-isopropyl-5-methyl-2,6-dioxo-1(2H)-pyrimidinyl]-benzoic acid isopropyl ester, 4-chloro-2-cyano-5-(1,2,4,5,6,7-hexahydro-1-methyl-2,4-dioxo-3H-cyclopenta[d]-pyrimidin-3-yl)-benzoic acid isopropyl ester, 4-bromo-2-cyano-5-(1,2,4,5,6,7-hexahydro-1-methyl-2,4-dioxo-3H-cyclopenta[d]-pyrimidin-3yl)-benzoic acid isopropyl ester, 2-cyano-5-[3,6-dihydro-3-methyl-4-trifluoromethyl-2,6-dioxo-1(2H)-pyrimidinyl]-benzoic acid methyl ester and the corresponding ethyl, n-propyl, n-butyl, sec-butyl, isobutyl, tert-butyl, methoxymethyl, 1-methoxyethyl, 2-methoxyethyl, 1-methoxypropyl, 1-ethoxyethyl, allyl, 1-methyl-2-propenyl, 1-ethyl-2-propenyl, 2-butenyl, propargyl, 2-butynyl, 1-methyl-2-propynyl and 1-ethyl-2-propynyl esters of that compound.

2-cyano-4-fluoro-5-[3,6-dihydro-3-methyl-4-trifluoromethyl-2,6-dioxo-1(2H)-pyrimidinyl]-benzoic acid methyl ester and the corresponding ethyl, n-propyl, n-butyl, sec-butyl, isobutyl, tert-butyl, methoxymethyl, 1-methoxyethyl, 2-methoxyethyl, 1-methoxypropyl, 1-ethoxyethyl, 2-methoxy-1-methylethyl, allyl, 1-methyl-2-propenyl, 1-ethyl-2-propenyl, 2-butenyl, propargyl, 2-butynyl, 1-methyl-2-propynyl and 1-ethyl-2-propynyl esters of that compound.

The process according to the invention for the preparation of compounds of formula I and their enol ethers and salts comprises a) for the preparation of those compounds of formula I wherein $R_1$ is hydrogen and $R_2$ is other than hydrogen and $R_4$ is other than chlorine, bromine or iodine and, if desired, metal salts of those compounds, subjecting to cyclisation, under basic conditions, a compound of the general formula

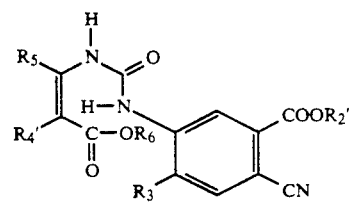

II wherein $R_3$ and $R_5$ are as defined above, $R_2'$ has the meaning given above for $R_2$ with the exception of hydrogen, $R_4'$ is hydrogen, fluorine or $C_1$-$C_4$alkyl or, together with $R_5$, is tri- or tetra-methylene, and $R_6$ is lower alkyl, preferably $C_1$-$C_4$alkyl, and, if desired, converting a possibly resulting metal salt form of the uracil derivative into the corresponding acid form ($R_1$=hydrogen) by treatment with an acid, b) for the preparation of those compounds of formula I wherein $R_1$ is hydrogen and $R_2$ is other than hydrogen, $R_4$ is other than chlorine, bromine or iodine and $R_5$ is other than $C_1$-$C_4$haloalkyl and, if desired, metal salts of those compounds, subjecting to cyclisation, under basic conditions, a compound of the general formula

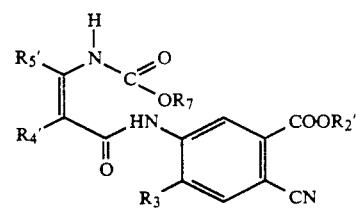

III wherein $R_2'$ and $R_3$ are as defined above, $R_4'$ is hydrogen, fluorine or $C_1$-$C_4$alkyl or, together with $R_5'$, is tri- or tetra-methylene, $R_5'$ is $C_1$-$C_4$alkyl or, together with $R_4'$, is tri-or tetra-methylene, and $R_7$ is lower alkyl, preferably $C_1$-$C_4$alkyl, and, if desired, converting a possibly resulting metal salt of the uracil derivative of formula I into the acid form ($R_1$=hydrogen) by treatment with an acid, c) for the preparation of those compounds of formula I wherein $R_1$ is $C_1$-$C_4$alkyl, $C_3$-$C_4$alkenyl, $C_3$-$C_4$alkynyl, $C_2$-$C_6$alkoxyalkyl or $C_1$-$C_4$haloalkyl, subjecting a uracil derivative of the general formula

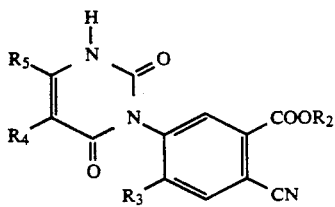

wherein $R_2$, $R_3$, $R_4$ and $R_5$ are as defined above, to alkylation with a corresponding alkylating agent comprising a $C_1$-$C_4$alkyl, $C_3$-$C_4$alkenyl, $C_3$-$C_4$alkynyl, $C_2$-$C_6$alkoxyalkyl or $C_1$-$C_4$haloalkyl group, d) for the preparation of all compounds of formula I and the enol ethers, treating a uracil derivative of the general formula

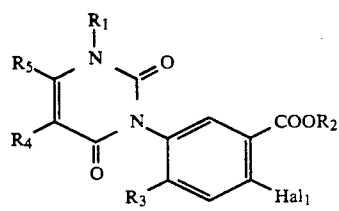

wherein $Hal_1$ is halogen, preferably chlorine or bromine, and $R_1$, $R_2$, $R_3$, $R_4$ und $R_5$ are as defined above, or the corresponding enol ether, with a metal cyanide, e) for the preparation of those compounds of formula I wherein $R_2$ is hydrogen and $R_5$ is other than $C_1$-$C_4$haloalkyl, and the enol ethers thereof, hydrolysing a benzoic acid ester of the general formula

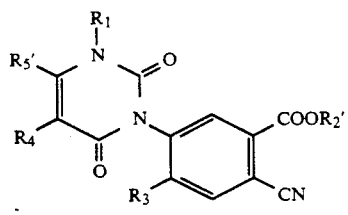

wherein $R_1$, $R_2'$, $R_3$, $R_4$ and $R_5'$ are as defined above, to form the corresponding benzoic acid, f) for the preparation of those compounds of formula I wherein $R_1$ and $R_2$ are each other than hydrogen and $R_5$ is other than $C_1$-$C_4$haloalkyl, and the corresponding enol ethers, esterifying a benzoic acid of the general formula

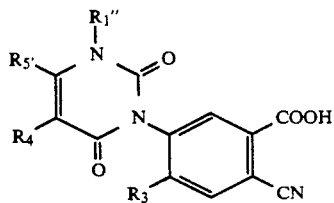

wherein $R_1''$ is $C_1$-$C_4$alkyl, $C_3$-$C_4$alkenyl, $C_3$-$C_4$alkynyl, $C_2$-$C_6$alkoxyalkyl or $C_1$-$C_4$haloalkyl and $R_3$, $R_4$ and $R_5'$ are as defined above, or the corresponding enol ether, it being possible for the benzoic acid or its enol ether to be in the form of a reactive derivative, with a hydroxy compound of the general formula $$HO-R_2' \qquad V$$

wherein $R_2'$ is as defined above, or with a reactive derivative of that hydroxy compound, g) for the preparation of those compounds of formula I wherein $R_1$ and $R_2$ are each other than hydrogen, and the enol ethers thereof, subjecting a benzoic acid ester of the general formula

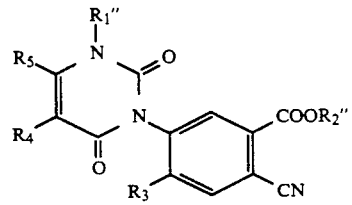

wherein $R_1''$, $R_3$, $R_4$ and $R_5$ are as defined above and $R_2''$ is $C_1$-$C_6$alkyl, $C_3$-$C_4$alkenyl, $C_3$-$C_4$alkynyl or $C_2$-$C_6$alkoxyalkyl, or the corresponding enol ether, to a transesterification reaction with a hydroxy compound of the above formula V, the reagent V having a higher boiling point than the respective alkanol, alkenol or alkynol $R_2''OH$, h) for the preparation of those compounds of formula I wherein $R_4$ is chlorine, bromine or iodine, and the corresponding enol ethers, chlorinating, brominating or iodinating a uracil derivative of the general formula

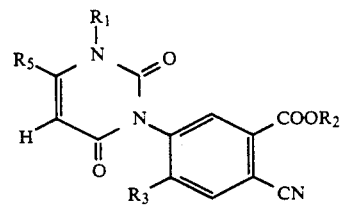

wherein $R_1$, $R_2$, $R_3$ and $R_5$ are as defined above, or the corresponding enol ether, i) for the preparation of the enol ethers of the compounds of formula I, treating a uracil derivative of the general formula

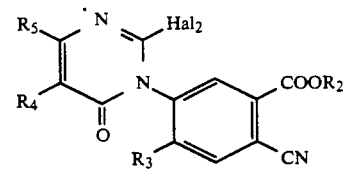

wherein $R_2$, $R_3$, $R_4$ and $R_5$ are as defined above, and $Hal_2$ is chlorine or bromine, with an alkanol, alkenol or alkynol $R_1'OH$ in the presence of an organic base, or with the corresponding alcoholate, alkenolate or alkynolate, respectively, of the general formula $$R_1'O^{\ominus}M^{\oplus} \qquad VII$$

wherein $R_1'$ is as defined above and $M^{\oplus}$ is an equivalent of a metal ion and, if desired, converting a resulting compound of formula I wherein $R_1$ and/or $R_2$ are (is) hydrogen into a salt.

The cyclisation according to process variant a) or b) can advantageously be carried out by treating the compound of formula II or III in an inert protic organic solvent, such as an alcohol, e.g. methanol, ethanol or isopropanol; in an inert aprotic organic solvent, such as an aliphatic or cyclic ether, e.g. 1,2-dimethoxyethane, tetrahydrofuran or dioxane, or an aromatic compound, e.g. benzene or toluene; in an inert aprotic polar organic solvent, e.g. dimethylformamide or dimethyl sulfoxide, it being possible, if desired, for such solvents to be used in a two-phase mixture with a hydrocarbon, e.g. n-hexane or toluene; or in water, with a base, at temperatures from $-78°$ C. to the reflux temperature of the reaction mixture. Suitable bases are preferably sodium alcoholates, alkali metal hydroxides, especially sodium hydroxide and potassium hydroxide, alkali metal carbonates, especially sodium carbonate and potassium carbonate, and sodium hydride. If an alkanol is used as solvent, then that solvent advantageously corresponds to the respective hydroxy compound $R_2'$—OH; by this means undesired competing trans-esterification reactions are avoided. If sodium hydride is used as base, the solvent is preferably an aliphatic or cyclic ether, dimethylformamide or dimethyl sulfoxide, it being possible for any of those solvents to be used in admixture with toluene.

When the cyclisation is complete, if one of the abovementioned bases or the like is used, the product is in the form of the corresponding alkali metal salt. This can be isolated and purified in a manner known per se, or the mixture can be acidified in order to isolate the respective compound of formula I itself. For that purpose preferably a mineral acid, such as hydrochloric acid, or a strong organic acid, such as acetic acid or p-toluenesulfonic acid, is used.

In process variant c), the term "alkylation" denotes the substitution of the hydrogen atom of the $N_1$ atom of the uracil nucleus by a $C_1-C_4$alkyl, $C_3-C_4$alkenyl, $C_3-C_4$alkynyl, $C_2-C_6$alkoxyalkyl or $C_1-C_4$haloalkyl group. There is advantageously used as alkylating agent a $C_1-C_4$alkyl, $C_3-C_4$alkenyl, $C_3-C_4$alkynyl or $C_2-C_6$alkoxyalkyl halide, especially the appropriate chloride or bromide, or sulfate, or a polyhalogenated $C_1-C_4$alkane, such as, e.g., chlorodifluoromethane, or a mono- or poly-halogenated alkene, such as, e.g., tetrafluoroethane.

The alkylation is advantageously carried out in the presence of an inert protic organic solvent, such as a lower alkanol, for example ethanol, if desired in admixture with water; an inert aprotic organic solvent, such as an aliphatic or cyclic ether, e.g. 1,2-dimethoxyethane, tetrahydrofuran or dioxane; a ketone, e.g. acetone or butan-2-one; or an inert aprotic polar organic solvent, e.g. dimethylformamide, dimethyl sulfoxide or acetonitrile, and also in the presence of a base, such as sodium hydride, an alkali metal hydroxide, especially sodium or potassium hydroxide, an alkali metal alcohlolate, especially sodium alcoholate, or an alkali metal carbonate or hydrogen carbonate, especially sodium carbonte, potassium carbonate, sodium hydrogen carbonate or potassium hydrogen carbonate, at temperatures from 0° C. to the reflux temperature of the reaction mixture, preferably at room temperature or, in the case of substitution of the hydrogen atom of the $N_1$ atom with a $C_1-C_4$haloalkyl group, preferably at temperatures from 50° C. to 100° C. In a preferred embodiment, the uracil derivative of romula I' is first of all treated with the base, such as sodiumi hydride, ethanolate or carbonte, in the solvent and, after a short reaction time, the halide is added in the same solvent. In a further embodiment, the uracil derivative I', together with a dialkyl sulfate, is reacted at reflux temperature in the presence of an alkali metal hydrogen carbonate, especially sodium or potassium hydrogen carbonate, in the solvent, e.g. acetone. The reaction is usually complete within a relatively short time or after a few hours, depending on the solvent used.

Process variant d) is an exchange reaction of the halogen substituent of the benzene nucleus. That halogen atom is thus replaced by the cyano group by means of the metal cyanide. The latter is especially a transition metal cyanide, preferably copper(I) cyanide. The reaction is advantageously carried out in the presence of an aprotic polar solvent, such as an alkylnitrile, e.g. acetonitrile, propionitrile or butyronitrile; an alkylurea, e.g. tetramethylurea; a dialkylamide, e.g. dimethylformamide; a dialkyl sulfoxide, e.g. dimethyl sulfoxide; N-methyl-2-pyrrolidone; 1,3-dimethyl-imidazolidin-2-one; 1,3-dimethyl-3,4,5,6-tetrahydro-2(1H)-pyrimidinone; or hexamethylphosphoric acid triamide, at elevated temperatures, that is from 80° C. to 200° C., preferably from 150° c. to 200° C. In the starting material I'', $R_4$ is preferably hyrogen or fluorine.

The hydrolysis of the benzoic acid ester I'' or the enol ether thereof according to process variant e) can be carried out according to methods known per se, especially using an organic solvent in aqueous solution, such as an aqueous alkanol, e.g. ethanol, or an aliphatic or cyclic ether, e.g. 1,2-dimethoxyethane, tetrahydrofuran or dioxan, in aqueous solution, and an inorganic base, such as lithium, sodium or potassium hydroxide, or an alkaline earth metal hydroxide, e.g. magnesium of calcium hydroxide, at temperatures from 0° C. to 60° C., preferably at room temperature.

Process variant f) is an esterification of benzoic acid or the enol ether or a reactive derivative thereof, which can be carried out according to methods known per se. For example, a salt of a benzoic acid of formula I''' or of the corresponding enol ether is reacted with a halide, especially the chloride, bromide or iodide, or the sulfate, mesylate or tosylate of the hydroxy compound V in an inert diluent at temperatures from room temperature to 100° C., e.g. at the reflux temperature of the reaction mixture, preferably in a temperature range from 40° C. to 70° C. Suitable salts of the benzoic acid of formula I''' or of the corresponding enol ether are especially alkali metal salts, e.g. the sodium, potassium or lithium salt, alkaline earth metal salts, e.g. the magnesium, calcium or barium salt, and salts with organic bases, such as tertiary amines, e.g. triethylamine, 1,5-diaza-bicyclo[4.3.0]non-5-ene, 1,8-diaza-bicyclo[5.4.0]undec-7-ene and 1,4-diaza-bicyclo[2.2.2]octane, with the alkali metal salts, especially the sodium salt and the potassium salt, being preferred. The diluents that can be used are preferably inert organic solvents, such as lower alkanols, e.g. ethanol, aliphatic and cyclic ethers, e.g. diethyl ether, tetrahydrofuran and dioxane, ketones, e.g. acetone and 2-butanone, dimethylformamide, dimethyl sulfoxide, acetonitrile and hexamethylphosphoric acid triamide. The salt can be produced in situ by reacting the acid with a suitable inorganic base, e.g. an alkali metal or alkaline earth metal carbonate, hydrogen carbonate, hydroxide or hydride, or organic base, to form the salt, which can then be reacted with the second reactant in the same reaction medium.

When an acid halide of the benzoic acid of formula I''' or of the corresponding enol ether is used as reactive derivative, it is advantageously reacted with the hydroxy compound of formula V in an inert organic solvent, such as an aliphatic or cyclic ether, e.g. diethyl ether, 1,2-dimethoxyethane, tetrahydrofuran or dioxane, an aliphatic or aromatic hydrocarbon, e.g. n-hexane, benzene or toluene, or a halogenated, especially chlorinated, hydrocarbon, e.g. methylene chloride, chloroform or carbon tetrachloride, at temperatures of approximately from $-20°$ C. to $100°$ C., preferably from $0°$ C. to $50°$ C. In addition, the reaction is advantageously carried out in the presence of an acid-binding agent, such as an organic base, e.g. triethylamine, pyridine, 4-dimethylaminopyridine, 1,5-diaza-bicyclo[4.3.0]non-5-ene, 1,8-diaza-bicyclo[5.4.0]undec-7-ene or 1,4-diaza-bicyclo[2.2.2]octane. The acid halide is preferably the acid chloride.

Other suitable reactive derivatives of the benzoic acid of formula I''' or of the corresponding enol ether are the corresponding O-acyl-1,3-dicyclohexylisourea and the corresponding N-acylimidazole or acid anhydride. Such derivatives can, like the acid halide, be reacted with the hydroxy compounds of formula V in order to obtain the desired benzoic acid esters. In those cases, however, the use of an acid-binding agent is not necessary.

The reaction according to process variant g) can advantageously be carried out by heating the benzoic acid ester of formula I'''' or its enol ether in excess hydroxy compound of formula V in the presence of a weakly basic catalyst, such as sodium cyanide or preferably tetraisopropyl or tetrapropyl orthotitanate, preferably at the reflux temperature of the reaction mixture. In the course of the reaction the radical $R_2''$ of the benzoic acid ester I'''' is replaced by the group $R_2'$ of the hydroxy compound V, the lower boiling alkanol, alkenol or alkynol $R_2''OH$ being freed and removed from the reaction mixture.

The chlorination or bromination according to process variant h) is advantageously carried out using elemental chlorine or sulfuryl chloride, or elemental bromine or sulfuryl bromide, respectively, in the presence of an inert organic solvent, such as acetic acid or a chlorinated aliphatic hydrocarbon, e.g. methylene chloride, chloroform or carbon tetrachloride, and in a temperature range from $0°$ C. to $60°$ C., preferably at room temperature. In addition, the reaction can be carried out with the assistance of an acid-binding agent, sodium acetate and tertiary amines, such as triethylamine, dimethylaniline and pyridine, being especially preferred acid-binding agents for that purpose.

The iodination according to that process variant is advantageously carried out using elemental iodine as iodinating agent and of a low-boiling aliphatic carboxylic acid, such as acetic acid, as solvent, at temperatures from approximately $0°$ C. to approximately $110°$ C., preferably at room temperature. In addition, it has proved advantageous to carry out the reaction in the presence of an acid, such as fuming nitric acid. When the reaction is complete, saturated aqueous sodium hydrogen sulfite solution can be added in order to remove excess iodine.

In process variant i), the term "metal ion" indicates especially an alkali metal ion, e.g. the sodium or potassium ion, or an alkaline earth metal ion, e.g. the calcium or magnesium ion. The sodium ion is the preferred metal ion. If the alkanol, alkenol or alkynol $R_1'OH$ is used, then the suitable organic base is especially pyridine.

The reaction is advantageously carried out in an excess of the corresponding alcohol $R_1'OH$ as diluent, and at temperatures from $0°$ C. to $50°$ C., preferably at room temperature.

If they cannot be prepared directly by the above-described cyclisation carried out under basic conditions, the desired salts of the compounds of formula I in which $R_1$ is hydrogen can alternatively be prepared from those compounds I in a manner known per se, for example by dissolving the compound of formula I in a solution of an appropriate organic or inorganic base. The salt formation is usually effected within a short time at room temperature. In one embodiment, the sodium salt is prepared by dissolving the uracil derivative I in aqueous sodium hydroxide solution at room temperature, using equivalent amounts of the uracil derivative and of sodium hydroxide. The solid salt can then be isolated by precipitation with a suitable inert solvent or by evaporating off the solvent. Another embodiment comprises introducing an aqueous solution of an alkali metal salt of the uracil derivative I into an aqueous solution of salt that has a metal ion other than an alkali metal ion, the second metal salt of the uracil derivative being produced. This embodiment is generally used to prepare uracil metal salts that are insoluble in water.

The compounds of formula I, enol ethers and salts obtained can be isolated and purified according to methods know per se. Also familiar to the person skilled in the art is the sequence in which possible combinations of process variants c) to h) are advantageously to be carried out so as to avoid possible undesired competing reactions.

If no specific synthesis for the isolation of pure isomers is carried out, the product may be obtained in the form of a mixture of two or more isomers. The isomers can be separated according to methods known per se. If desired, for example, pure optically active isomers can also be produced by synthesis from corresponding optically active starting materials.

The starting materials of formula II, which are novel, can be prepared in a manner known per se, e.g. in accordance with the following Reaction Schemes 1 [Methods aa), bb) and cc)]:

Reaction Schemes 1

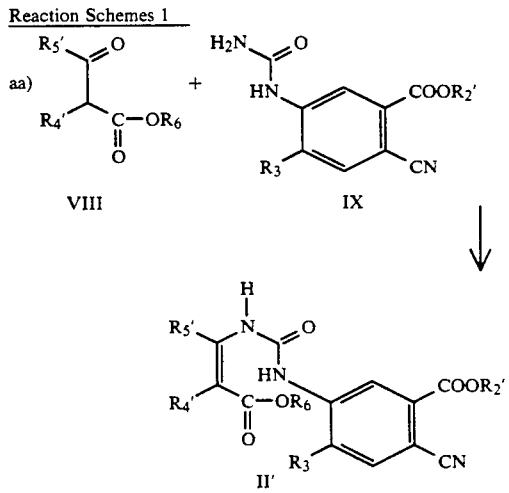

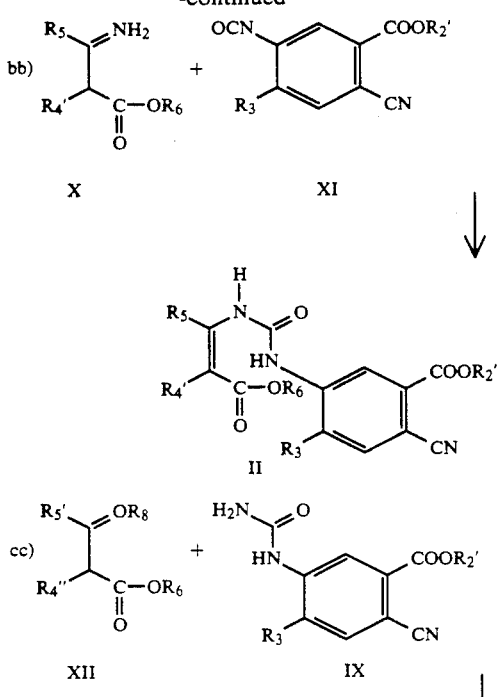

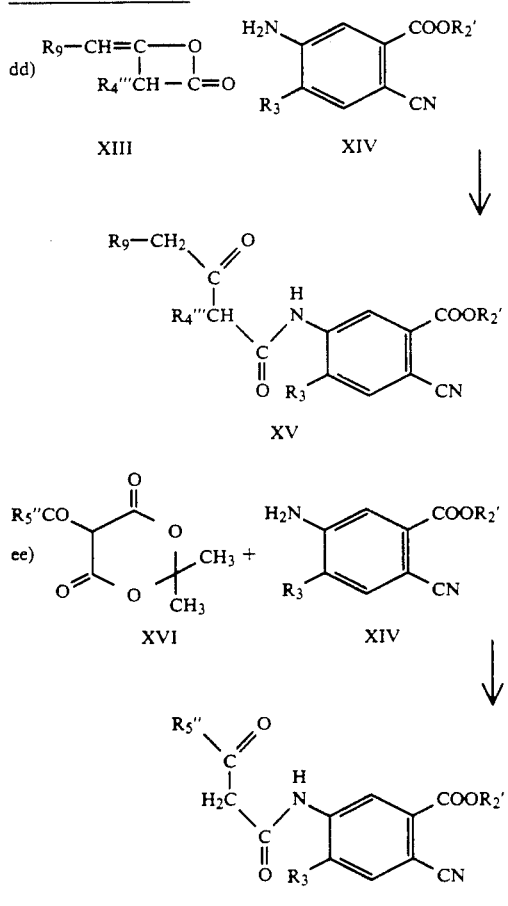

In the above reaction schemes, $R_{2'}$, $R_3$, $R_{4'}$, $R_5$, $R_{5'}$ and $R_6$ have the meanings given hereinbefore; $R_{4''}$ is hydrogen or $C_1$-$C_4$alkyl or, together with $R_{5'}$, is tri- or tetramethylene; and $R_8$ is lower alkyl, preferably $C_1$-$C_4$alkyl.

Method aa) is advantageously carried out by reacting the compounds of formulae VIII and IX with each other in a substantially anhydrous diluent in the presence of an acid catalyst at elevated temperature. Suitable diluents are especially organic solvents that form azeotropes with water, such as aromatic compounds, e.g. benzene, toluene and xylenes; halogenated hydrocarbons, such as methylene chloride, chloroform, carbon tetrachloride and chlorobenzene; and aliphatic and cyclic ethers, such as 1,2-dimethoxyethane, tetrahydrofuran and dioxane, and suitable acidic catalysts are especially strong mineral acids, such as sulfuric acid and hydrochloric acid; organic acids, such as p-toluenesulfonic acid; phosphorus-containing acids, such as orthophosphoric acid and polyphosphoric acid; and acidic cation exchangers, such as "Amberlyst 15" (Fluka). The reaction is generally carried out in a temperature range from approximately 70° C. to 120° C., preferably at the reflux temperature of the reaction mixture. Under those reaction conditions the desired rapid removal of the water formed during the reaction is achieved.

The reaction according to Method bb) is advantageously carried out in the presence of a substantially anhydrous aprotic organic solvent, such as an aliphatic or cyclic ether, e.g. diethyl ether, 1,2-dimethoxyethane, tetrahydrofuran or dioxane, an aliphatic or aromatic hydrocarbon, e.g. n-hexane, benzene, toluene or a xylene; or a halogenated, aliphatic hydrocarbon, e.g. methylene chloride, chloroform, carbon tetrachloride or 1,2-dichloroethane; and also where appropriate in the presence of a base, especially an organic tertiary base, such as triethylamine or pyridine, it being possible for the latter to be used both as solvent and base, or a metal hydride, such as sodium or potassium hydride. The reaction temperatures are preferably in the range of approximately from −80° C. to 50° C., temperatures of from −30° C. to room temperature being especially preferred.

The reaction according to Method cc) is advantageously carried out in an inert water-miscible organic solvent, such as an aliphatic or cyclic ether, e.g. 1,2-dimethoxyethane, tetrahydrofuran or dioxane, or a lower alkanol, such as ethanol, at temperatures from 50° C. to 100° C., preferably at the reflux temperature of the reaction mixture, or in an aromatic solvent, such as benzene, toluene or a xylene, in the presence of an acidic catalyst, such as hydrochloric acid or p-toluenesulfonic acid, at temperatures from 50° C. to 100° C., preferably from 60° C. to 80° C.

The starting materials of formula III are also novel and can be prepared in a manner known per se, e.g. in accordance with the following Reaction Schemes 2 [Methods dd), ee) and ff)]:

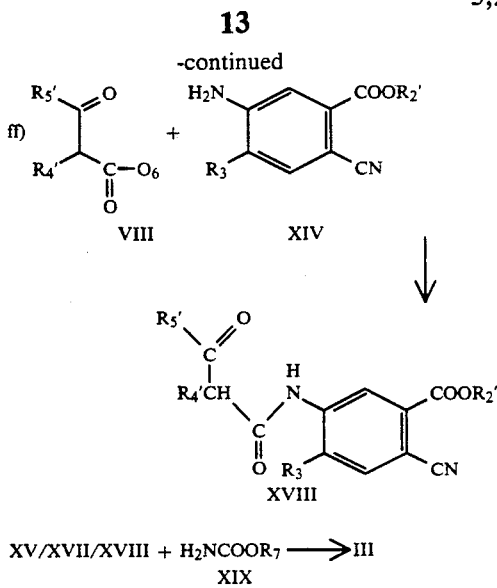

XV/XVII/XVIII + H$_2$NCOOR$_7$ $\longrightarrow$ III
XIX

In the above Reaction Schemes, R$_{2'}$, R$_3$, R$_{4'}$, R$_{5'}$, R$_6$ and X have the meanings given hereinbefore; R$_{4''}$ is hydrogen or C$_1$–C$_4$alkyl; R$_{5''}$ is C$_1$–C$_4$alkyl; and R$_9$ is hydrogen or C$_1$–C$_3$alkyl.

The reaction of the amine of formula XIV with the diketene of formula XIII according to Method dd) is advantageously carried out in an anhydrous inert aprotic solvent, such as a halogenated hydrocarbon, e.g. methylene chloride, chloroform, carbon tetrachloride or chlorobenzene, an aromatic hydrocarbon, e.g. benzene, toluene or a xylene, or an aliphatic or cyclic ether, e.g. diethyl ether, 1,2-dimethoxyethane, tetrahydrofuran or dioxane, in the presence of a basic catalyst, such as 4-pyrrolidinopyridine, 4-dimethylaminopyridine, 1,4-diazabicyclo[2.2.2]octane, 1,5-diazabicyclo[4.3.0]non-5-ene, 1,8-diazabicyclo[5.4.0]undec-7-ene or diethylamine. Since the reaction is exothermic, it is generally carried out in a temperature range from −10° C. to 50° C., preferably at room temperature.

The reaction of the compounds of formulae XVI and XIV with each other in accordance with Method ee) is advantageously carried out in an anhydrous inert aprotic solvent at temperatures from approximately 70° C. to 140° C, preferably from 100° C. to 120° C. There are suitable as such solvents especially aromatic compounds, e.g. benzene, toluene and xylenes; halogenated hydrocarbons, e.g. carbon tetrachloride, trichloroethane, tetrachloroethane and chlorobenzene; and aliphatic and cyclic ethers, e.g. dibutyl ether, 1,2-dimethoxyethane, tetrahydrofuran and dioxane.

The reaction according to Method ff) is an aminolysis, which is advantageously carried out in an anhydrous solvent, or without solvent [see, for example, J. Soc. Dyes Col. 42, 81 (1926), Ber. 64, 970 (1931) and J.A.C.S. 70, 2402 (1948)] at elevated temperature. Suitable solvents are especially inert aprotic solvents, such as unsubstituted or halogenated aromatic compounds, e.g. toluene, xylenes and chlorobenzenes. The reaction is generally carried out in a temperature range from approximately 130° C. to 160° C. Where appropriate the reaction is in addition carried out in the presence of a basic catalyst, e.g. a higher-boiling amine [see, for example, Helv. Chim. Acta 11, 779 (1928) and U.S. Pat. No. 2,416,738] or pyridine.

The subsequent reaction of the compound of formula XV, XVII or XVIII prepared in that manner with the carbamic acid lower alkyl ester of formula XIX is advantageously carried out in a substantially anhydrous diluent and in the presence of an acidic catalyst at elevated temperature. Suitable diluents are especially organic solvents that form azeotropes with water, such as aromatic compounds, e.g. benzene, toluene and xylenes; cyclic aliphatic compounds, such as cyclohexane; and halogenated hydrocarbons, such as carbon tetrachloride and chlorobenzene, and suitable acidic catalysts are especially strong mineral acids, such as sulfuric acid; organic acids, such as orthophosphoric acid and polyphosphoric acid; and acidic cation exchangers, such as "Amberlyst 15" (Fluka). The reaction is generally carried out in a temperature range from approximately 70° C. to 150° C., preferably at the reflux temperature of the reaction mixture. Under those reaction conditions the desired rapid removal of the water formed during the reaction is achieved.

The starting materials of formula IV, the corresponding enol ethers and their preparation are for the most part described in European Patent Publications Nos. 195 346 and 260 621. Those starting materials IV and enol ethers for which the preparation is not described may be prepared analogously to the known starting materials.

The starting materials of formula VI used in process variant i) can be prepared by halogenating the corresponding uracil derivative of the above formula I'. The halogenating agent used for the halogenation is especially thionyl chloride, phosphorus pentachloride or phosphorus oxychloride, or phosphorus pentabromide or phosphoryl bromide. If desired a mixture of phosphorus pentachloride and phosphorus oxychloride, or of phosphorus pentabromide and phosphoryl bromide, may be used, it being possible for excess phosphorus oxychloride or phosphoryl bromide, respectively, to act as diluent. The chlorination or bromination can be carried out in the presence of an inert diluent, especially an aprotic organic solvent, such as an aliphatic or aromatic hydrocarbon, e.g. n-hexane, benzene, toluene or a xylene; a halogenated aliphatic hydrocarbon, e.g. methylene chloride, chloroform or 1,2-dichloroethane; a halogenated aromatic hydrocarbon, e.g. chlorobenzene, or a tertiary amine, e.g. N,N-dimethylaniline, but this is not necessary if phosphorus oxychloride or phosphoryl bromide is used as halogenating agent. If the halogenating agent used is thionyl chloride it has proved advantageous to add a catalytic amount of dimethylformamide. The reaction temperatures generally range from 0° C. to the reflux temperature of the reaction mixture, preferably from 80° C. to 120° C.

The uracil derivatives of formulae I', I'', I''', I'''' and I''''' and enol ethers used as starting materials in process variants c), e), f), g) and h) are sub-groups of compounds of formula I and the enol ethers thereof. The remaining starting materials and reagents involved in the process variants and in the reaction schemes are either known or can be prepared by methods that are known per se.

The compounds of formula I and their enol ethers and salts (referred to in the following collectively as "compounds of the invention" or "active ingredients") are suitable for controlling, preventing or eliminating plant growth, especially undesired plant growth. The compounds of the invention possess especially herbicidal properties and are suitable for controlling weeds, including grass weeds, for example *Abutilon theophrasti, Amaranthus retroflexus, Agropyron repens, Alopecurus*

*myosuroides, Avena fatua, Bromus inermis, Cyperus esculentus, Ipomoea purpurea, Poa annua, Sorghum halepense, Stellaria media, Cassia obtusifolia, Chenopodium album, Chrysanthemum segetum, Datura stramonium, Digitaria sanguinalis, Echinochloa crus-galli, Galium aparine, Matricaria chamomilla, Setaria faberii, Sinapis arvensis* and *Xanthium pennsylvanicum*, in diverse crops of useful plants, for example rape, soybean, cotton, rice, wheat and maize crops, but especially in cotton crops. In addition, the compounds are both preemergence and postemergence herbicides. Furthermore, the compounds of the invention can be used to control undersired plant growth, e.g. in potatoes, cotton plants, sunflowers, seed vegetables and water weeds. They may be used, for example, as burning-off agents to facilitate the harvesting of potatoes and cotton. preferably 1 g to 200 g of the compound of the invention/ha, is sufficient to achieve the desired herbicidal effect.

The concentration required for the desired effect can be determined by tests. It is dependent on the nature of the action, the stage of development of the cultivated plant and of the weed and on the application (place, time, method) and can vary widely as a function of those parameters.

The weed control composition according to the invention is characterised in that it comprises an effective amount of at least one compound of formula I, as defined above, or of an enol ether or salt thereof, togethr with formulation adjuvants. The composition advantageously comprises at least one of the following formulation adjuvants: solid carriers; solvents or dispersants; surfactants (wetting agents and emulsifiers); dispersants (without surface-active action); and stabilisers. Using those and other adjuvants, those compounds, that is to say the herbicidal active ingredients, can be converted into customary formulations, such as dusts, powders, granules, solutions, emulsions, suspensions, emulsifiable concentrates, pastes and the like.

The compounds of formula I and their enol ethers are in general water-insoluble, whereas the salts, especially the alkali metal salts and ammonium salts, are generally water-soluble; they can be formulated according to the methods customary for water-insoluble and water-soluble compounds using the appropriate formulation adjuvants. The preparation of the compositions can be carried out in a manner known per se, e.g. by mixing the active ingredient in question with solid carriers, by dissolving or suspending in suitable solvents or dispersants, optionally using surfactants as wetting agents or emulsifiers and/or dispersants, by diluting ready-prepared emulsifiable concentrates with solvents or dispersants etc.

Suitable solid carriers are essentially natural mineral substances, such as chalk, dolomite, limestone, argillaceous earths and silicic acid and salts thereof (for example diatomaceous earth, kaolin, bentonite, talcum, attapulgite and montmorillonite); synthetic mineral substances, such as highly dispersed silicic acid, aluminium oxide and silicates; organic materials, such as cellulose, starch, urea and synthetic resins; and fertilisers, such as phosphates and nitrates, it being possible for such carriers to be, for example, in the form fof powders or granules.

Suitable solvents and dispersants are essentially aromatic compounds, such as benzene, toluene, xylenes and alkylnaphthalenes; chlorinated aromatic compounds and chlorinated aliphatic hydrocarbons, such as chlorobenzenes, chloroethylenes and methylene chloride; aliphatic hydrocarbons, such as cyclohexane and paraffins, e.g. petroleum fractions; alcohols, such as butanol and glycol, and their ethers and esters; ketones, such as acetone, methyl ethyl ketone, methyl isobutyl ketone and cyclohexanone; and strongly polar solvents or dispersants, such as dimethylformamide, N-methylpyrrolidone and dimethyl sulfoxide, such solvents preferably having flash points of at least 30° C. and boiling points of at least 50° C., and water. Also suitable as solvents and dispersants are so-called liquefied gaseous extenders or carriers, which are products that are gaseous at room temperature under normal pressure. Examples of such products are especially aerosol propellant gases, such as hydrocarbons, e.g. propane and isobutane, and halogenated hydrocarbons, e.g. dichlorodifluoromethane. If the weed control composition of the invention is in the form of a pressurised gas pack, then advantageously a solvent is used in addition to the propellant gas.

The surfactants (wetting agents and emulsifiers) may be non-ionic compounds, such as condensation products of fatty acids, fatty alcohols or fat-substituted phenols with ethylene oxide; fatty acid esters and ethers of sugars or of polyhydric alcohols; the products obtained from sugars or polyhydric alcohols by condensation with ethylene oxide; block polymers of ethylene oxide and propylene oxide; or alkyldimethylamine oxides.

The surfactants may also be anionic compounds, such as soaps; fatty sulfate esters, e.g. dodecyl sodium sulfate, octadecyl sodium sulfate and cetyl sodium sulfate; alkyl-sulfonates, arylsulfonates and fatty aromatic sulfonates, such as alkylbenzene sulfonates, e.g. calcium dodecylbenzene sulfonate, and butylnaphthalene sulfonates; and more complex fatty sulfonates, e.g. the amide condensation products of oleic acid and N-methyltaurin, and the sodium sulfonate of dioctyl succinate.

Finally, the surfactants may be cationic compounds, such as alkyldimethylbenzylammonium chlorides, dialkyldimethylammonium chlorides, alkyltrimethylammonium chlorides and ethoxylated quaternary ammonium chlorides.

Suitable dispersants (without surface-active action) are essentially lignin, sodium and ammonium salts of lignosulfonic acids, sodium salts of maleic acid anhydride/diisobutylene copolymers, sodium and ammonium salts of sulfonated polycondensation products of naphthalene and formaldehyde, and sulfite waste liquors.

As dispersants, which are suitable especially as thickeners and anti-settling agents, there may be used, e.g., methylcellulose, carboxymethylcellulose, hydroxyethylcellulose, polyvinyl alcohol, alginates, caseinates and blood albumin.

Examples of suitable stabilisers are acid-binding agents, e.g. epichlorohydrin, phenylglycidyl ethers and soya epoxides; antioxidants, e.g. gallic acid esters and butylhydroxytoluene; UV absorbers, e.g. substituted benzophenones, diphenylacrylonitrile acid esters and cinnamic acid esters; and deactivators, e.g. salts of ethylenediaminetetraacetic acid and polyglycols.

The weed control compositions according to the invention may comprise, in addition to the active ingredients of the invention, synergists and other active ingredients, e.g. insecticides, acaricides, fungicides, plant-growth regulators and fertilisers. Such combination compositions are suitable for strengthening the activity or broadening the activity spectrum.

The weed control compositions according to the invention generally comprise from 0.01 to 95% by weight, preferably from 0.5 to 75% by weight, of one or more compounds according to the invention as active ingredient(s). They may, for example, be in a form that is suitable for storage and transport. In such formulations, e.g. emulsifiable concentrates, the active ingredient concentration is normally in the higher range, preferably from 1 to 50 % by weight, especially from 10 to 20% by weight. Those formulations can then be diluted, e.g. with identical or different inert substances, to the active ingredient concentrations suitable for practical use, that is to say preferably approximately 0.01 to 10% by weight, especially approximately 0.005 to 5% by weight. The active ingredient concentrations may, however, also be lower or higher.

As mentioned above, the preparation of the weed control compositions according to the invention can be carried out in a manner known per se.

In order to prepare pulverulent compositions, the active ingredient, that is to say at least one compound of the invention, may be mixed with a solid carrier, e.g. by grinding together; or the solid carrier may be impregnated with a solution or suspension of the active ingredient and then the solvent or dispersant, as the case may be, removed by evaporation, heating or filtering with suction under reduced pressure. Such pulverulent compositions can be made readily wettable with water by adding surfactants or dispersants, so that they can be converted into aqueous suspensions that are suitable, e.g., as spray compositions.

The active ingredient may also be mixed with a surfactant and a solid carrier to form a wettable powder that is dispersible in water, or may be mixed with a solid pregranulated carrier to form a granular product.

If desired, the active ingredient may be dissolved in a water-immiscible solvent, such as, for example, a high-boiling hydrocarbon, that advantageously comprises dissolved emulsifier so that the solution is self-emulsifying when water is added. Alternatively, the active ingredient may be mixed with an emulsifier and the mixture then diluted with water to the desired concentration. Further, the active ingredient may be dissolved in a solvent and then mixed with an emulsifier. Such a mixture may also be diluted with to the desired concentration. Emulsifiable concentrates and ready-for-use emulsions are obtained in this manner.

The use of the weed control compositions according to the invention, to which the present invention also relates, may be in accordance with customary application methods, such as sprinkling, spraying, dusting, pouring or scattering. The method according to the invention of controlling weeds comprises treating the substrates to be protected against weeds and/or the weeds with a compound of the invention or with a weed control composition of the invention.

The following Examples are to illustrate the invention further.

I. Preparation of the compounds of formula I

EXAMPLE 1

A mixture of 50.0 g of 2-chloro-5-[3,6-dihydro-3,4-dimethyl-2,6-dioxo-1(2H)-pyrimidinyl]-4-fluorobenzoic acid isopropyl ester and 25.4 g of copper(I) cyanide in 225 ml of dimethyl-3,4,5,6-tetrahydro-2(1H)-pyrimidinone is heated for 2.5 hours at 195° C. under nitrogen. The mixture is then cooled to room temperature and 2 l of ethyl acetate are added. The mixture is then poured onto 1.3 l of water and 300 ml of 32% hydrochloric acid, and the whole is stirred for 45 minutes at room temperature until two distinct layers have formed. The organic phase is removed, washed twice with 200 ml of water each time and dried over anhydrous sodium sulfate. Concentration by evaporation of the organic solution yields crystalline 2-cyano-5-[3,6-dihydro-3,4-dimethyl-2,6-dioxo-1(2H)-pyrimidinyl]-4-fluorobenzoic acid isopropyl ester, m.p. 188°–200° C.

EXAMPLES 2–10

The compounds of formula I listed in the following Table 1 are obtained analogously to the process described in Example 1 by treating the corresponding uracil derivative of formula IV with copper(I) cyanide:

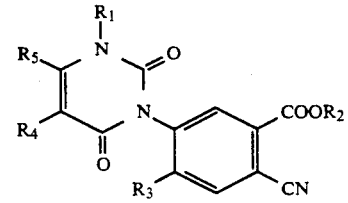

| Example | $R_1$ | $R_2$ | $R_3$ | $R_4$ | $R_5$ | Physical data |
|---|---|---|---|---|---|---|
| 2 | $CH_3$ | $CH(CH_3)_2$ | H | H | $CF_3$ | m.p. 125–127° C. |
| 3 | $CH_3$ | $CH(CH_3)_2$ | F | H | $CF_3$ | m.p. 130–132° C. |
| 4 | $CH_3$ | $CH(CH_3)_2$ | F | H | $C_2F_5$ | m.p. 116–118° C. |
| 5 | $CH_3$ | $CH(CH_3)_2$ | F | —$(CH_2)_4$— | | m.p. 170–172° C. |
| 6 | $CH_3$ | $CH(CH_3)_2$ | F | —$(CH_2)_3$— | | m.p. 164–166° C. |
| 7 | $CH_3$ | $CH(CH_3)_2$ | F | F | $CF_3$ | m.p. 133–136° C. |
| 8 | $CH_3$ | $CH_3$ | H | H | $CF_3$ | m.p. 167–168° C. |
| 9 | $CHF_2$ | $CH(CH_3)_2$ | F | —$(CH_2)_4$— | | m.p. 142–145° C. |
| 10 | $CHF_2$ | $CH(CH_3)_2$ | F | H | $CH_3$ | m.p. 146–148° C. |

EXAMPLE 11

A solution of 30.5 g of 2-cyano-5-[3,6-dihydro-3,4-dimethyl-2,6-dioxo-1(2H)-pyrimidinyl]-4-fluorobenzoic acid isopropyl ester (see Example 1) in 150 ml of methanol is maintained at 1°–3° C. for 15 minutes with 4.0 g of sodium hydroxide in 50 ml of water and then stirred for 23 hours. The solution is substantially concentrated by evaporation under reduced pressure and the residue is adjusted to a pH value of 2 with 2N hydrochloric acid. The resulting precipitate is filtered off with suction and subsequently washed with n-hexane to yield 2-cyano-5-[3,6-dihydro-3,4-dimethyl-2,6-dioxo-1(2H)-pyrimidinyl]-4-fluorobenzoic acid, m.p. 232° C. (with decomposition).

EXAMPLE 12

A solution of 2-cyano-5-[3,6-dihydro-3,4dimethyl-2,6-dioxo-1(2H)-pyrimidinyl]-4-fluorobenzoic acid (see Example 9) in 30 ml of absolute dimethylformamide is stirred for 2 hours at room temperature with 0.29 g of a 55% sodium hydride dispersion. A solution of 1.1 g of propargyl bromide in 10 ml of absolute dimethylformamide is then added dropwise over a period of 10 minutes and the reaction mixture is subsequently stirred for 3 hours.

The mixture is then dissolved in 100 ml of ethyl acetate, the solution is washed thoroughly with water, and the organic phase is dried over anhydrous sodium sulfate and concentrated to dryness by evaporation under reduced pressure. The residue is purified by chromatography on a silica gel column using n-hexane/ethyl acetate (3:7) as eluant to yield 2-cyano-5-[3,6-dihydro-3,4-dimethyl-2,6-dioxo-1(2H)-pyrimidinyl]-4-fluorobenzoic acid propargyl ester, m.p. 174°-177° C.

EXAMPLES 13-15

Analogously to the process described in Example 12, the compounds of formula I listed in the following Table 2 are obtained by esterifying 2-cyano-5-[3,6-dihydro-3,4-dimethyl-2,6-dioxo-1(2H)-pyrimidinyl]-4-fluorobenzoic acid (see Example 11) with allyl bromide, methyl iodide and 2-methoxyethyl bromide, respectively:

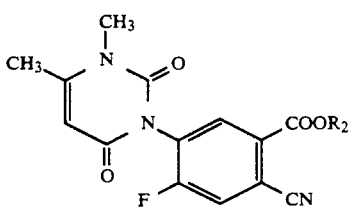

TABLE 2

| Example | $R_2$ | Physical data |
|---|---|---|
| 13 | allyl | m.p. 143-148° C. |
| 14 | methyl | m.p. 244-246° C. |
| 15 | 2-methoxyethyl | m.p. 126-130° C. |

EXAMPLE 16

A mixture of 3.0 g of finely pulverised 2-cyano-5-[3,6-dihydro-3,4-dimethyl-2,6-dioxo-1(2H)-pyrimidinyl]-4-fluorobenzoic acid, 30 ml of freshly distilled thionyl chloride and 3 drops of dimethylformamide is heated at reflux temperature for 1 hour with stirring, after which a clear solution has formed. The mixture is then concentrated to dryness by evaporation to yield 2-cyano-5-[3,6-dihydro-3,4-dimethyl-2,6-dioxo-1(2H)-pyrimidinyl]-4-fluorobenzoic acid chloride, m.p. 160° C., which is used, unpurified, as the starting material in the next reaction step.

A solution of 1.5 g of 1,2,3,6-tetrahydrobenzyl alcohol and 0.015 g of 4-dimethylaminopyridine in 2.5 g of pyridine is added dropwise, at room temperature, to a solution of 3.8 g of 2-cyano-5-[3,6-dihydro-3,4-dimethyl-2,6-dioxo-1(2H)-pyrimidinyl]-4-fluorobenzoic acid chloride in 130 ml of tetrahydrofuran. After heating the reaction mixture for 12 hours at 60° C., the resulting suspension is substantially concentrated by evaporation under reduced pressure and the residue is dissolved in ethyl acetate.

The organic solution is washed thoroughly with water, the organic phase is dried over anhydrous sodium sulfate and concentrated to dryness by evaporation under reduced pressure, and the residue is purified by chromatography on a silica gel column using n-hexane/ethyl acetate (3:7) as eluant to yield 2-cyano-5-[3,6-dihydro-3,4-dimethyl-2,6-dioxo-1(2H)-pyrimidinyl]-4-fluorobenzoic acid 1,2,3,6-tetrahydrobenzyl ester, mass spectrum (m/e): 397(15)M+.

BIOLOGICAL EXAMPLES

EXAMPLE B1: PREEMERGENCE HERBICIDAL ACTION

Immediately after sowing the test plants (a number of weeds, both monocotyledonous and dicotyledonous) in seed trays in the greenhouse, an aqueous spray mixture, corresponding to a rate of application of 3 kg of active ingredient/hectare, is used to treat the soil surface.

The test compounds are preferably formulated as emulsifiable concentrates (EC) and diluted with water to the desired concentration immediately before application. Insoluble compounds are formulated as wettable powders (WP) using kaolin as inert carrier. The wettable powder is suspended in water immediately before application.

The concentrations of active ingredient in g/ha refer to the soil surface in the containers unless indicated otherwise. The spraying volume is 1000 l/ha (corresponding to 100 ml/m$^2$).

The plant seeds are sown in plastics plant pots of various sizes containing heat-sterilised (steam-treated) soil (agricultural soil 2.6% peat, 20% clay, 30% silt, 47% sand). The plants are kept in the greenhouse at average temperature (17°-25° C. in winter, 18°-35° C. in summer) (humidity 30-90%). The length of the photoperiod is 13 to 16 hours/day and is, if necessary, supplemented by artificial light (15 000 to 18 000 lux). The artificial lighting is also automatically activated if the intensity of the daylight is inadequate.

After 3 weeks the herbicidal action is evaluated by comparison with an untreated control group using an eleven-stage linear evaluation scheme (necrosis, chlorosis, reduction, deformation) (2=80-100% damage, 1=30-79% damage, 0=0-29% damage)

TABLE B1

| | preemergence herbicidal action: | | | | | | | | |
|---|---|---|---|---|---|---|---|---|---|
| Example | SORG | ECHI | AVEN | ALOP | CHEN | STEL | ABUT | DATU | MATR | CASS |
| 01 | 2 | 2 | 2 | 2 | 2 | 2 | 2 | 2 | 2 | 2 |
| 02 | 2 | 2 | 2 | 2 | 2 | 2 | 2 | 2 | 2 | 2 |
| 03 | 2 | 2 | 2 | 2 | 2 | 2 | 2 | 2 | 2 | 2 |
| 04 | 2 | 2 | 2 | 2 | 2 | 2 | 2 | 2 | 2 | 2 |
| 05 | 2 | 2 | 2 | 2 | 2 | 2 | 2 | 2 | 2 | 2 |
| 06 | 2 | 2 | 2 | 2 | 2 | 2 | 2 | 2 | 2 | 2 |
| 07 | 2 | 2 | 2 | 2 | 2 | 2 | 2 | 2 | 2 | 2 |
| 08 | 2 | 2 | 2 | 2 | 2 | 2 | 2 | 2 | 2 | 2 |
| 09 | 2 | 2 | 2 | 2 | 2 | 2 | 2 | 2 | 2 | 2 |
| 10 | 2 | 2 | 2 | 2 | 2 | 2 | 2 | 2 | 2 | 2 |
| 12 | 2 | 2 | 2 | 2 | 2 | 2 | 2 | 2 | 2 | 2 |
| 13 | 2 | 2 | 2 | 2 | 2 | 2 | 2 | 2 | 2 | 2 |
| 14 | 2 | 2 | 2 | 2 | 2 | 2 | 2 | 2 | 2 | 2 |

TABLE B1-continued

| | preemergence herbicidal action: | | | | | | | | | |
|---|---|---|---|---|---|---|---|---|---|---|
| Example | SORG | ECHI | AVEN | ALOP | CHEN | STEL | ABUT | DATU | MATR | CASS |
| 15 | 2 | 2 | 2 | 2 | 2 | 2 | 2 | 2 | 2 | 2 |

Key to the Table:
SORG *Sorghum halopense*
ECHI *Echinochloa crus-galli*
AVEN *Avena fatua*
ALOP *Alopecurus myosuroides*
CHEN *Chenopodium album*
STEL *Stellaria media*
ABUT *Abutilon theophrasti*
MATR *Matricaria chamomilla*
CASS *Cassia media*

EXAMPLE B2

Postemergence herbicidal action (contact herbicide)

A number of weeds, both monocotyledonous and dicotyledonous, are treated postemergence (at the 2- to 6-leaf stage) with an aqueous active ingredient dispersion at a rate of 3 kg of active ingredient per hectare.

The test compounds are preferably formulated as emulsifiable concentrates (EC) and diluted with water to the desired concentration immediately before application. Insoluble compounds are formulated as wettable powders (WP) using kaolin as inert carrier. The wettable powder is suspended in water immediately before application.

The concentrations of active ingredient in g/ha refer to the soil surface in the containers unless indicated otherwise. The spraying volume is 500 l/ha.

The plant seeds are sown in plastics plant pots of various sizes containing heat-sterilised (steam-treated) soil ('Optima' soil 80% peat, 20% loess). The plants are kept in the greenhouse at average temperature (17°-25° C. in winter, 18°-35° C. in summer) (atmospheric humidity 30-90%). The length of the photoperiod is 13 to 16 hours/day and is, if necessary, supplemented by artificial light (15 000 to 18 000 lux). The artificial lighting is also automatically activated if the intensity of the daylight is inadequate.

After 3 weeks the herbicidal action is evaluated by comparison with an untreated control group using an eleven-stage linear evaluation scheme (necrosis, chlorosis, reduction, deformation) (2=80-100% damage, 1=30-79% damage, 0=0-29% damage).

TABLE B2

| | postemergence herbicidal action: | | | | | | | | | |
|---|---|---|---|---|---|---|---|---|---|---|
| Example | SORG | ECHI | AVEN | ALOP | CHEN | STEL | ABUT | DATU | MATR | CASS |
| 01 | 2 | 2 | 1 | 1 | 2 | 1 | 2 | 2 | 2 | 2 |
| 02 | 2 | 2 | 2 | 2 | 2 | 2 | 2 | 2 | 2 | 2 |
| 03 | 2 | 2 | 2 | 2 | 2 | 2 | 2 | 2 | 2 | 2 |
| 04 | 2 | 2 | 2 | 2 | 2 | 2 | 2 | 2 | 2 | 2 |
| 05 | 2 | 2 | 2 | 1 | 2 | 2 | 2 | 2 | 2 | 2 |
| 06 | 2 | 2 | 2 | 1 | 2 | 2 | 2 | 2 | 2 | 2 |
| 07 | 2 | 2 | 2 | 2 | 2 | 2 | 2 | 2 | 2 | 2 |
| 08 | 2 | 2 | 2 | 2 | 2 | 2 | 2 | 2 | 2 | 2 |
| 10 | 2 | 2 | 2 | 2 | 2 | 2 | 2 | 2 | 2 | 2 |
| 13 | 2 | 2 | 2 | 1 | 2 | 1 | 2 | 2 | 2 | 1 |

Formulation examples of active substances of the formula I
(% = percent by weight)

| 1. Wettable powder | a) | b) | c) |
|---|---|---|---|
| Active subst. from Examples 1-15 | 20% | 50% | 0.5% |
| Na ligninsulfonate | 5% | 5% | 5% |
| Na lauryl sulfate | 3% | — | — |
| Na diisobutylnaphthalenesulfonate | — | 6% | 6% |
| Octylphenol polyethylene glycol ether (7-8 mol of EO) | — | 2% | 2% |
| Highly-disperse silica | 5% | 27% | 27% |
| Kaolin | 67% | — | — |
| Sodium chloride | — | — | 59.5% |

The active substance is thoroughly mixed with the additives and thoroughly ground in a suitable mill. This gives wettable powders which can be diluted with water to give suspensions of any desired concentration.

| 2. Emulsion concentrates | a) | b) |
|---|---|---|
| Active subst. from Examples 1-15 | 10% | 1% |
| Ca dodecylbenzenesulfate | 3% | 3% |
| Octylphenol polyethylene glycol ether (4-5 mol of EO) | 3% | 3% |
| Castor oil polyethylene glycol ether (36 mol of EO) | 4% | 4% |
| Cyclohexanone | 30% | 10% |
| Xylene mixture | 50% | 79% |

Emulsions of any desired concentration can be prepared from such concentrates by diluting them with water.

| 3. Dusts | a) | b) |
|---|---|---|
| Active subst. from Examples 1-15 | 0.1% | 1% |
| Talc | 99.9% | — |
| Kaolin | — | 99% |

Ready-to-use dusts are obtained by intimately mixing the carrier with the active substance.

| 4. Extruder granules | a) | b) |
|---|---|---|
| Active subst. from Examples 1-15 | 10% | 1% |
| Na ligninsulfonate | 2% | 2% |

| -continued | | |
|---|---|---|
| 4. Extruder granules | a) | b) |
| Carboxymethylcellulose | 1% | 1% |
| Kaolin | 87% | 96% |

The active substance is mixed with the additives, and the mixture is ground and moistened with water. This mixture is extruded and subsequently dried in a stream of air.

| 5. Coated granules | |
|---|---|
| Active subst. from Examples 1-15 | 3% |
| Polyethylene glycol (MW 200) | 3% |
| Kaolin | 94% |

The kaolin is moistened with polyethylene glycol and the finely-ground active substance is applied uniformly thereto in a mixer. Dust-free coated granules are obtained in this manner.

| 6. Suspension concentrate | a) | b) |
|---|---|---|
| Active subst. from Examples 1-15 | 5% | 40% |
| Ethylene glycol | 10% | 10% |
| Nonylphenol polyethylene glycol ether (15 mol of EO) | 1% | 6% |
| Na ligninsulfonate | 5% | 10% |
| Carboxymethylcellulose | 1% | 1% |
| 37% aqueous formaldehyde solution | 0.2% | 0.2% |
| Silicone oil in the form of a 75% aqueous emulsion | 0.8% | 0.8% |
| Water | 77% | 32% |

The finely-ground active substance is mixed intimately with the additives. This gives a suspension concentrate, from which suspensions of any desired concentration can be prepared by diluting it with water.

| 7. Salt solution | |
|---|---|
| Active subst. from Examples 1-15 | 5% |
| Isopropylamine | 1% |
| Octylphenol polyethylene glycol ether (78 mol of EO) | 3% |
| Water | 91% |

The compounds of the formula I are employed as such or preferably as compositions together with the auxiliaries customary in formulation technology, and they are therefore processed in a known manner to give, for example, emulsion concentrates, directly sprayable or dilutable solutions, dilute emulsions, sprayable powders, soluble powders, dusts, granules, and also encapsulations, for example in polymeric substances. The application methods, such as spraying, atomising, dusting, scattering or pouring, as well as the type of compositions are selected to suit the intended aims and the prevailing circumstances.

What is claimed is:

1. A compound of the formula

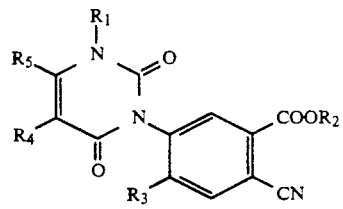

wherein
R$_1$ is hydrogen, C$_1$-C$_4$alkyl, C$_3$-C$_4$alkenyl, C$_3$-C$_4$alkynyl, C$_2$-C$_6$alkoxyalkyl or C$_1$-C$_4$haloalkyl,
R$_2$ is hydrogen, C$_1$-C$_6$alkyl, C$_2$-C$_6$alkoxyalkyl, C$_4$-C$_7$cycloalkenyl-C$_1$-C$_4$alkyl that is unsubstituted or ring-substituted by from 1 to 3 C$_1$-C$_3$alkyl groups, C$_3$-C$_4$alkenyl, C$_4$-C$_7$cycloalkenyl-C$_3$-C$_5$alkenyl that is unsubstituted or ring-substituted by from 1 to 3 C$_1$-C$_3$alkyl groups, phenyl-C$_3$-C$_5$alkenyl wherein the phenyl group is unsubstituted or substituted by from 1 to 3 halogen atoms, C$_1$-C$_3$alkyl, C$_1$-C$_3$haloalkyl, C$_1$-C$_3$alkoxy, C$_1$-C$_3$alkylthio, C$_2$-C$_4$alkanoyl, C$_2$-C$_4$alkoxycarbonyl, C$_1$-C$_3$alkylsulfonyl, nitro or cyano, C$_3$-C$_4$alkynyl, C$_4$-C$_7$cycloalkenyl-C$_3$-C$_5$alkynyl that is unsubstituted or ring-substituted by from 1 to 3 C$_1$-C$_3$alkyl groups, or phenyl-C$_3$-C$_5$alkynyl wherein the phenyl group is unsubstituted or substituted by from 1 to 3 halogen atoms, C$_1$-C$_3$alkyl, C$_1$-C$_3$haloalkyl, C$_1$-C$_3$-alkoxy, C$_1$-C$_3$alkylthio, C$_2$-C$_4$alkanoyl, C$_2$-C$_4$alkoxycarbonyl, C$_1$-C$_3$alkylsulfonyl, nitro or cyano,
R$_3$ is hydrogen or halogen,
R$_4$ is hydrogen, halogen or C$_1$-C$_4$alkyl and
R$_5$ is C$_1$-C$_4$alkyl or C$_1$-C$_4$haloalkyl, or
R$_4$ and R$_5$ together are tri- or tetra-methylene, with the proviso that, when R$_5$ is C$_1$-C$_4$haloalkyl, R$_1$ is other than C$_1$-C$_4$haloalkyl and R$_2$ is other than hydrogen, and when R$_1$ is C$_1$-C$_4$haloalkyl, R$_2$ is other than hydrogen, C$_1$-C$_4$-alkyl, C$_3$-C$_4$alkenyl, C$_3$-C$_4$alkynyl and C$_2$-C$_6$alkoxyalkyl, or the corresponding enol ether of such a compound of formula I wherein R$_1$ is other than hydrogen, C$_1$-C$_4$alkyl, C$_3$-C$_4$alkynyl and C$_1$-C$_4$haloalkyl, or a salt of such a compound of formula I wherein R$_1$, R$_2$ or both are hydrogen.

2. A compound according to claim 1, wherein R$_1$ is C$_1$-C$_4$alkyl.

3. A compound according to claim 1, wherein R$_2$ is C$_1$-C$_6$alkyl, C$_2$-C$_6$alkoxyalkyl, C$_3$-C$_4$alkenyl or C$_3$-C$_4$alkynyl.

4. A compound according to any one of claims 1 to 3, wherein R$_3$ is hydrogen or fluorine.

5. A compound according to claim 1, wherein R$_4$ is hydrogen or fluorine and R$_5$ is C$_1$-C$_4$alkyl or trifluoromethyl, or R$_4$ and R$_5$ together are tri- or tetra-methylene.

6. A compound according to claim 1, selected from the group consisting of
2-cyano-5-(1,2,4,5,6,7-hexahydro-1-methyl-2,4-dioxo-3H-cyclopenta[d]pyrimidin-3-yl)-benzoic acid isopropyl ester,
2-cyano-4-fluoro-5-(1,2,4,5,6,7-hexahydro-1-methyl-2,4-dioxo-3H-cyclopenta[d]-pyrimidin-3-yl)-benzoic acid isopropyl ester,
2-cyano-5-[1,4,5,6,7,8-hexahydro-1-methyl-2,4-dioxo-3(2H)-quinazolinyl]-benzoic acid isopropyl ester, 2-cyano-4-fluoro-5-[1,4,5,6,7,8-hexahydro-1-methyl-2,4-dioxo-3(2H)-quinazolinyl]-benzoic acid isopropyl ester, 2-cyano-4-fluoro-5-[3,6-dihydro-3,4-dimethyl-2,6-dioxo-1(2H)-pyrimidinyl]-benzoic acid isopropyl ester, 2-cyano-5-[3,6-dihydro-3-methyl-4-trifluoromethyl-2,6-dioxo-1(2H)-pyrimidinyl]-benzoic acid isopropyl ester and 2-cyano-5-[3,6-dihydro-3-methyl-4-trifluoromethyl-2,6-dioxo-1(2H)-pyrimidinyl]-4-fluorobenzoic acid isopropyl ester.

7. A weed control composition which comprises an effective amount of at least one compound of the formula

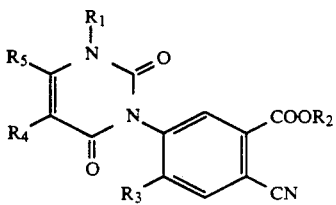

I wherein $R_1$ is hydrogen, $C_1$-$C_4$alkyl, $C_3$-$C_4$alkenyl, $C_3$-$C_4$alkynyl, $C_2$-$C_6$alkoxyalkyl or $C_1$-$C_4$haloalkyl, $R_2$ is hydrogen, $C_1$-$C_6$alkyl, $C_2$-$C_6$alkoxyalkyl, $C_4$-$C_7$cycloalkenyl-$C_1$-$C_4$alkyl that is unsubstituted or ring-substituted by from 1 to 3 $C_1$-$C_3$alkyl groups, $C_3$-$C_4$alkenyl, $C_4$-$C_7$cycloalkenyl-$C_3$-$C_5$alkenyl that is unsubstituted or ring-substituted by from 1 to 3 $C_1$-$C_3$alkyl groups, phenyl-$C_3$-$C_5$alkenyl wherein the phenyl group is unsubstituted or substituted by from 1 to 3 halogen atoms, $C_1$-$C_3$alkyl, $C_1$-$C_3$haloalkyl, $C_1$-$C_3$alkoxy, $C_1$-$C_3$alkylthio, $C_2$-$C_4$alkanoyl, $C_2$-$C_4$alkoxycarbonyl, $C_1$-$C_3$alkyl-sulfonyl, nitro or cyano, $C_3$-$C_4$alkynyl, $C_4$-$C_7$cycloalkenyl-$C_3$-$C_5$alkynyl that is unsubstituted or ring-substituted by from 1 to 3 $C_1$-$C_3$alkyl groups, or phenyl-$C_3$-$C_5$alkynyl wherein the phenyl group is unsubstituted or substituted by from 1 to 3 halogen atoms, $C_1$-$C_3$alkyl, $C_1$-$C_3$haloalkyl, $C_1$-$C_3$-alkoxy, $C_1$-$C_3$alkylthio, $C_2$-$C_4$alkanoyl, $C_2$-$C_4$alkoxycarbonyl, $C_1$-$C_3$alkylsulfonyl, nitro or cyano, $R_3$ is hydrogen or halogen, $R_4$ is hydrogen, halogen or $C_1$-$C_4$alkyl and $R_5$ is $C_1$-$C_4$alkyl or $C_1$-$C_4$haloalkyl, or $R_4$ and $R_5$ together are tri- or tetra-methylene, with the proviso that, when $R_5$ is $C_1$-$C_4$haloalkyl, $R_1$ is other than $C_1$-$C_4$haloalkyl and $R_2$ is other than hydrogen, and when $R_1$ is $C_1$-$C_4$haloalkyl, $R_2$ is other than hydrogen, $C_1$-$C_4$-alkyl, $C_3$-$C_4$alkenyl, $C_3$-$C_4$alkynyl and $C_2$-$C_6$alkoxyalkyl, or of the enol ether of such a compound I wherein $R_1$ is other than hydrogen, $C_1$-$C_4$alkyl, $C_3$-$C_4$alkynyl and $C_1$-$C_4$haloalkyl, or of a salt of such a compound wherein $R_1$, $R_2$ or both are hydrogen, and a formulation adjuvant.

8. A weed control composition according to claim 7, which comprises an effective amount of at least one compound selected from the group consisting of 2-cyano-5-(1,2,4,5,6,7-hexahydro-1-methyl-2,4-dioxo-3H-cyclopenta[d]pyrimidin-3-yl)-benzoic acid isopropyl ester, 2-cyano-4-fluoro-5-(1,2,4,5,6,7-hexahydro-1-methyl-2,4-dioxo-3H-cyclopenta[d]pyrimidin-3-yl)-benzoic acid isopropyl ester, 2-cyano-5-[1,4,5,6,7,8-hexahydro-1-methyl-2,4-dioxo-3(2H)-quinazolinyl]-benzoic acid isopropyl ester, 2-cyano-4-fluoro-5-[1,4,5,6,7,8-hexahydro-1-methyl-2,4-dioxo-3(2H)-quinazolinyl]-benzoic acid isopropyl ester, 2-cyano-4-fluoro-5-[3,6-dihydro-3,4-dimethyl-2,6-dioxo-1(2H)-pyrimidinyl]-benzoic acid isopropyl ester, 2-cyano-5-[3,6-dihydro-3-methyl-4-trifluoromethyl-2,6-dioxo-1(2H)-pyrimidinyl]-benzoic acid isopropyl ester and 2-cyano-5-[3,6-dihydro-3-methyl-4-trifluoromethyl-2,6-dioxo-1(2H)-pyrimidinyl]-4-fluorobenzoic acid isopropyl ester, and formulation adjuvants.

9. A method of controlling weeds which comprises treating the substrates to be protected against weeds and/or the weeds with an effective amount of a compound according to claim 1 or of a composition containing said compound.

* * * * *